United States Patent [19]

Narayanan et al.

[11] 4,003,909
[45] Jan. 18, 1977

[54] [(1,2,4-OXADIAZOL-3-YL)PHENYL]CARBAMIC OR THIOCARBAMIC ACID ESTERS

[75] Inventors: Venkatachala L. Narayanan, Hightstown; Rudiger D. Haugwitz, Titusville, both of N.J.

[73] Assignee: E. R. Squibb & Sons, Inc., Princeton, N.J.

[22] Filed: Apr. 9, 1975

[21] Appl. No.: 566,595

Related U.S. Application Data

[63] Continuation-in-part of Ser. No. 490,643, July 22, 1974, abandoned.

[52] U.S. Cl. .................. 260/307 G; 260/250 B; 260/256.4 R; 260/256.5 R; 260/287 CE; 260/294.8 E; 260/295 CA; 260/302 H; 424/250; 424/251; 424/258; 424/263; 424/270; 424/272

[51] Int. Cl.² ........................ C07D 271/06

[58] Field of Search .................. 260/307 G

[56] References Cited

UNITED STATES PATENTS 3,270,028  8/1966  Palazzo ............... 260/307

*Primary Examiner*—Raymond V. Rush
*Attorney, Agent, or Firm*—Lawrence S. Levinson; Merle J. Smith; Stephen B. Davis

[57] ABSTRACT

Compounds of the formula

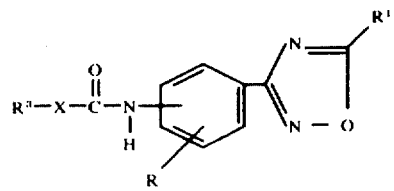

and their acid-addition salts wherein X is O or S; R is hydrogen, lower alkyl, phenyl, chloro, bromo, trifluoromethyl, lower alkoxy, phenoxy, or di(lower alkyl)amino; $R^1$ is hydrogen, lower alkyl, phenyl, substituted-phenyl, cycloalkyl, or heterocyclic; and $R^3$ is lower alkyl, substituted-lower alkyl, cycloalkyl, lower alkenyl, lower alkynyl, phenyl, or substituted phenyl; are disclosed. These compounds exhibit anthelmintic and antibacterial and antifungal activity.

10 Claims, No Drawings

[(1,2,4-OXADIAZOL-3-YL)PHENYL]CARBAMIC OR THIOCARBAMIC ACID ESTERS

This application is a continuation-in-part of application Ser. No. 490,643 filed July 22, 1974, now abandoned.

BACKGROUND OF THE INVENTION

Palazzo in U.S. Pat. No. 3,270,028 discloses [4-(5-chloromethyl-1,2,4-oxadiazol-3-yl)phenyl]carbamic acid, ethyl ester as an intermediate which is reacted so as to replace the chloromethyl group by a hydroxymethyl or acetoxymethyl group.

SUMMARY OF THE INVENTION

This invention relates to compounds of the formula:

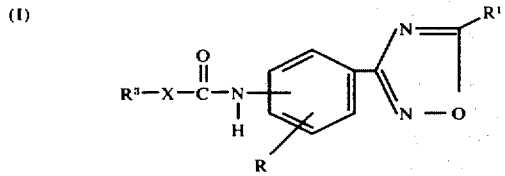

(I)

and thier pharmaceutically acceptable acid addition salts which are useful as anthelmintic agents, antibacterial and antifungal agents.

X is oxygen or sulfur.

R is hydrogen, lower alkyl, phenyl, chloro, bromo, trifluoromethyl, lower alkoxy, phenoxy or di(lower alkyl)amino.

$R^1$ is hydrogen, lower alkyl, phenyl, substituted-phenyl, cycloalkyl, or heterocyclic.

$R^3$ is lower alkyl, substituted-lower alkyl, cycloalkyl, lower alkenyl, lower alkynyl, phenyl, or substituted phenyl.

In addition, this invention encompasses the methods for preparing said (substituted-aminophenyl)oxadiazoles, compositions containing said (substituted-aminophenyl)oxadiazoles and methods for using said compositions.

The term "lower alkyl" is intended to mean a straight or branched hydrocarbon fragment of from one to ten carbon atoms, preferably 1 to 4, such as methyl, propyl, t-butyl, etc.

Cycloalkyl includes ring systems of 3 to 6 carbon atoms such as cyclopropyl, cyclopentyl, cyclohexyl, etc.

The term "lower alkoxy" is intended to mean a lower alkyl group linked through a single bond to oxygen.

The terms "lower alkenyl" and "lower alkynyl" are intended to mean a straight or branched unsaturated hydrocarbon fragment of from two to ten carbon atoms, preferably 2 to 4, having at least one double bond, e.g. allyl, or at least one triple bond, e.g. 2-propynyl, respectively.

The term "substituted-phenyl" is intended to include a phenyl radical having one or two substituents selected from fluoro, chloro, bromo, iodo, amino, nitro, trifluoromethyl, lower alkyl and lower alkoxy or three methoxy substituents.

The term "substituted-lower alkyl" is intended to include an alkyl radical as defined above having one or more substituents selected from chloro, bromo, fluoro and iodo, preferably one, two or three chloro, bromo, or fluoro substituents such as 2,2,2-trichloroethyl, trifluoromethyl, etc.

The term "heterocyclic" is intended to mean a five or six membered heterocyclic ring containing from one to three heteroatoms, selected from the group consisting of oxygen, nitrogen and sulfur. Examples of such "heterocyclic rings" are thiophene, furan, thiazole, isothiazole, pyridine, pyrrole, pyrazine, quinoline, imidazole, oxazole, pyrimidine, etc. Also within the meaning of this term are said heterocycles substituted by a lower alkyl or lower alkoxy group, i.e. N-methylpyrrole. The heterocyclic ring is attached at any available carbon atom as for example 2-, 3-, or 4-pyridyl; 2- or 3-thienyl; 2- or 3-furyl; etc.

The term "pharmaceutically acceptable acid-addition salts" is intended to mean the relatively nontoxic acid addition salts, such as the hydrochloride, hydrobromide, sulfate, phosphate, acetate, maleate, citrate, etc.

DETAILED DESCRIPTION OF THE INVENTION

The compounds of formula I are prepared by reacting an aminophenyloxadiazole of formula II with a substituted-haloformate or halothioformate of formula III

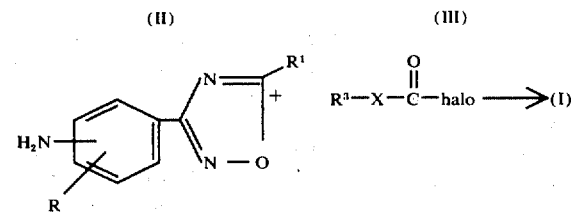

wherein halo can be preferably either chloro or bromo. The reaction is performed at a temperature of from about 20° to about 100° C in an organic solvent such as benzene, acetone, dioxane, or acetonitrile and in the presence of an acid binding agent such as potassium carbonate, triethylamine, etc. By employing these neutral solvents without an acid binding agent the product is isolated as the acid-addition salt. It is possible to employ a solvent which also serves as an acid binding agent, for example, pyridine, picolines, and lutidines. The product of formula I can be purified by recrystallization from solvents such as benzene, ethyl acetate, chloroform, and acetonitrile or by chromatography with an alumina IV column.

The aminophenyloxadiazoles of formula II wherein $R^1$ is hydrogen, lower alkyl, cycloalkyl, phenyl, or substituted phenyl are disclosed in copending application Ser. No. 347,313 now abandoned in favor of continuation-in-part Ser. No. 487,497, now U.S. Pat. No. 3,910,942, and the compounds of formula II wherein $R^1$ is heterocyclic are disclosed in copending application Ser. No. 347,312, now U.S. Pat. No. 3,853,893. As set forth in these applications, the compounds of formula II are prepared in the following manner.

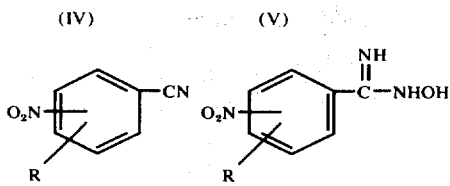

The nitrobenzonitriles of formula IV are converted to amidoximes of the formula V by treatment with an acid salt of hydroxylamine, such as the hydrochloride, sulfate or phosphate in the presence of an acid acceptor, such as sodium or potassium carbonate. The reaction is generally conducted in an aqueous or non-aqueous alcohol solvent of up to four carbon atoms at from about room temperature to the reflux temperature of the solvent for periods of from one to 48 hours, preferably about 24 hours.

The amidoximes of the formula V are converted to the oxadiazoles of the formula VI wherein $R^1$ is hydrogen by a variety of methods.

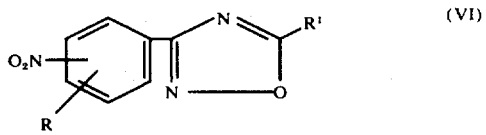

a. An amidoxime of the formula V is dissolved in an excess of tri(lower alkyl)orthoformate, preferably triethyl, and heated between about 100° C to about 146° C for about 0.5 to about 24 hours. The product of the formula VI, either precipitates out, and is separated by filtration, or the excess tri(lower alkyl)orthoformate is removed and the product washed with an organic solvent, such as petroleum ether.

b. An amidoxime of the formula V is heated to about 100° C with about an equimolar quantity of formic acid for from about one half a minute to ten minutes.

c. An amidoxime of the formula V is cyclized by reaction with two molar equivalents of a complex of dimethylformamide-phosphorus oxychloride in an ether such as tetrahydrofuran, diethyl ether, etc. at temperatures of from about −10° to about room temperature for from one minute to three hours. After removal of the solvent and washing with water, the desired compound of formula VI is obtained.

d. An amidoxime of the formula V is dissolved in an inert organic solvent, preferably an ether, at depressed temperatures (about −10° C to about 10° C) and reacted with a mixed anhydride of the formula

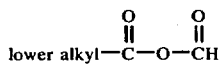

and stirred for a period of from about five minutes to about 3 hours.

Oxadiazoles of the formula VI wherein $R^1$ is lower alkyl, cycloalkyl, heterocyclic, phenyl or substituted phenyl are prepared by heating a compound of the formula:

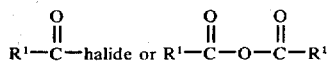

with a compound of formula V.

In many instances the acylating agent may be used in excess thus also serving as the solvent medium; however, generally an inert organic solvent, such as benzene or ether is employed. The temperature range generally employed is either the refluxing temperature of the solvent or about 100° C whichever is the lesser, and the time ranges from about a few minutes to about eighteen hours. This reaction is preferably conducted in the presence of a catalytic amount of $BF_3$-etherate.

Compounds of formula VI are converted to those of the formula II in poor yield, utilizing reducing agents such as $PtO_2/H_2$, $Na_2S_2O_4/CH_3OH$, $Pd/H_2$, $N_2H_4$, $NaBH_2S_3/THF$, and $Pd/C$.

Surprisingly, catalytic reduction using about 5% Pd/C in the presence of about 2–5 equivalents of an acid, such as hydrochloric acid or sulfuric acid, gives good yields of amino compounds.

Preferred compounds of formula I are those wherein R is hydrogen or chlorine; and $R^1$ is hydrogen, lower alkyl, cycloalkyl, phenyl, substituted phenyl, thienyl, thiazolyl, pyridyl, furyl, or N-methylpyrryl; and especially where the oxadiazole is located on the phenyl ring para with respect to the carbamic acid ester function.

More preferred are those wherein R is hydrogen; $R^1$ is hydrogen, cyclopropyl, cyclohexyl, phenyl, 3,4,5-trimethoxyphenyl, 4-chlorophenyl, thienyl, thiazolyl, pyridyl, furyl, or N-methylpyrryl; and $R^3$ is alkyl of 1 to 4 carbons, alkenyl of 2 to 4 carbons, alkynyl of 2 to 4 carbons, cycloalkyl of 3 to 6 carbons, substituted-alkyl of 1 to 4 carbons, phenyl, or substituted phenyl.

The most preferred compounds are those wherein R and $R^1$ are hydrogen and $R^3$ is alkyl of 1 to 4 carbons, allyl, 2-propynyl, cyclopropyl, phenyl, 2,2,2-trichloroethyl or 4-fluorophenyl.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. They are useful in treating infections caused by haemonchus, ancylostoma, ostertagia, trichostrongylus, cooperia, nematodirus, bunostomum, strongylorides, oesophagostomum, trichiuris and moniezia. In treating domesticated animals, the compounds are given orally and may be mixed with a nontoxic, edible carrier to form a feed supplement, or be administered in unit dosage forms such as powders, capsule, tablet, boluses, drenches, etc.

In general, the compounds of formula I exhibit anthelmintic activity when administered to animals in a daily dose of about 10 to about 200 mg per kilogram of animal body weight. It is preferred to employ in the range of 20–100 mg per kilogram of body weight per day. The compounds may be given in a single dose or divided into a plurality of smaller doses. When the compounds are to be employed primarily as prophylactic agents for the prevention of helminthic infections, the preferred daily dose level is, of course, lower than the therapeutic level is, preferably in the range of about 2–20 mg per kilogram of body weight.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent (5–50%, preferably 10–30%) intimately dispersed in or admixed with an inert carrier or diluent, i.e. one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredient in a feed which is inert to said anthelmintic compounds so as to give feeds having concentrations of anthelmintic agent of from 0.1–2%.

The compounds of formula I also have activity against gram-positive bacteria and fungi, and are useful in mammalian species for the treatment and prevention of (a) superficial dermatoses, bacterial or fungal diseases due to species of Staphylococcus, Streptococcus, Corynebacterium, Erysipelothrix, Candida, Trichophyton, Microsporum and Epidermophyton, (b) deep mycoses, fungal diseases due to Candida, Cryptococcus, Blastomyces, Histoplasma and similar organisms, and (c) thrush, fungal disease due to Candida species, principally Candida albicans.

In general, the compounds of this invention exhibit antibacterial and antifungal activity when applied as a 0.5–2.0% cream or ointment to the skin of an affected mammal for 2 weeks or more; given orally in daily doses of about 10–200 milligrams per kilogram of body weight; given by injection in daily doses of about 10–50 milligrams per kilogram of body weight; or given intravaginally. The compounds are formulated for all forms of administration using conventional pharmaceutical techniques.

The following examples are provided for illustrative purposes and include particular features of the invention; however, the examples should not be construed as limiting the invention, many variations of which are possible without departing from the spirit or scope thereof. All temperatures are in degrees centigrade.

EXAMPLE 1

[4-(1,2,4-Oxadiazol-3-yl)phenyl]carbamic acid, methyl ester a. p-Nitrobenzamidoxime A solution of 29.6 g. (0.20 mole) of p-nitrobenzonitrile, 13.9 g. (0.20 mole) of hydroxylamine HCl, 13.8 g. (0.10 mole) of $K_2CO_3$ in 700 ml. of ethanol and 70 ml. of water is refluxed for 20 hours, cooled and diluted with 200 ml. of water. After removal of the ethanol by distillation in vacuo, the product is collected by filtration, washed with water and dried to yield 21.6 g. (60%).

b. 3-(4-Nitrophenyl)-1,2,4-oxadiazole 2 cc. of boron trifluoride etherate is added to a solution of 25.3 g. (0.14 mole) of p-nitrobenzamidoxime, from part (a), in 187 cc. of triethyl orthoformate. The resulting mixture is stirred at ambient temperature overnight. White crystals are formed which are filtered, washed with cyclohexane, and dried to yield 21.0 g. of 3-(4-nitrophenyl)-1,2,4-oxadiazole; m.p. 164°–165°.

c. 3-(4-Aminophenyl)-1,2,4-oxadiazole

A mixture of 25.6 g. (0.134 mole) of 3-(4-nitrophenyl)-1,2,4-oxadiazole, from part (b), 22.8 ml. (0.268 mole) of hydrochloric acid, and 700 ml. of ethanol containing 10% Pd/C is reduced on a Parr hydrogenator for 1 hour. The catalyst and the resulting amine salt are filtered and washed with a solution of 39 ml. (0.268 mole) of triethylamine in 100 ml. of ethanol. The filtrate and washings are combined and dried. Tetrahydrofuran (THF) is added to the residue, and the insoluble triethylamine hydrochloride is filtered and washed with THF. The filtrate is dried up to yield 17 g. (79%) of crude product; m.p. 97°–100°. 3 g. of the crude product is dissolved in benzene and passed through 60 g. of Alumina IV. The eluant is concentrated to yield 1.43 g. of white needles of 3-(4-aminophenyl)-1,2,4-oxadiazole; m.p. 100°–101°.

d. [4-(1,2,4-Oxadiazol-3-yl)phenyl]carbamic acid, methyl ester 1.41 g. (0.015 moles) of methyl chloroformate is added to a mixture of 1.91 g. (0.012 mole) of 3-(4-aminophenyl)-1,2,4-oxadiazole, from part (c), and 2.07 g. (0.015 mole) of potassium carbonate in 50 cc. of dioxane. The resulting mixture is heated at reflux temperature for 15 minutes and then concentrated to dryness. The residue is crystallized from benzene-ethyl acetate to yield 1.39 g. (53%) of [4-(1,2,4-oxadiazol-3-yl)phenyl]carbamic acid, methyl ester; m.p. 174.5°–176°.

EXAMPLE 2

[4-(1,2,4-Oxadiazol-3-yl)phenyl]thiocarbamic acid, methyl ester

Following the procedure of example 1, but substituting an equivalent amount of methyl chlorothioformate for the methyl chloroformate in part (d), [4-(1,2,4-oxadiazol-3-yl)-phenyl]thiocarbamic acid, methyl ester is obtained.

EXAMPLE 3

[4-(1,2,4-Oxadiazol-3-yl)phenyl]carbamic acid, phenyl ester 2.34 g. (0.015 mole) of phenyl chloroformate is added to a mixture of 1.91 g. (0.012 mole) of 3-(4-aminophenyl)-1,2,4-oxadiazole, from example 1c, and 2.07 g. (0.015 mole) of potassium carbonate in 50 cc. of dioxane. The resulting mixture is heated at reflux temperature for 15 minutes and then concentrated to dryness. The residue is crystallized from benzene to yield 1.58 g. (47%) of [4-(1,2,4-oxadiazol-3-yl)-phenyl]carbamic acid, phenyl ester; m.p. 157°–158°.

EXAMPLE 4

[4-(1,2,4-Oxadiazol-3-yl)phenyl]thiocarbamic acid, phenyl ester

Following the procedure of example 3, but substituting an equivalent amount of phenyl chlorothioformate for the phenyl chloroformate, [4-(1,2,4-oxadiazol-3-yl)phenyl]thiocarbamic acid, phenyl ester is obtained.

EXAMPLE 5

[4-(1,2,4-Oxadiazol-3-yl)phenyl]carbamic acid, 2,2,2-trichloroethyl ester 3.16 g. (0.015 mole) of 2,2,2-trichloroethyl chloroformate is added to a mixture of 1.61 g. (0.01 mole) of 3-(4-aminophenyl)-1,2,4-oxadiazole, from example 1c, and 2.07 g. (0.015 mole) of potassium carbonate in 50 cc. of dioxane. The resulting mixture is stirred for sixteen hours at ambient temperature and then evaporated to dryness. The residue is chromatographed on an Alumina IV column and eluted with 5% $CHCl_3$-benzene to yield 1.85 g. (55%) of [4-(1,2,4-oxadiazol-3-yl)phenyl]carbamic acid, 2,2,2-trichloroethyl ester; m.p. 108°–110°.

EXAMPLE 6

[4-(1,2,4-Oxadiazol-3-yl)phenyl]thiocarbamic acid, 2,2,2-trichloroethyl ester

Following the procedure of example 5, but substituting an equivalent amount 2,2,2-trichloroethyl chlorothioformate for the 2,2,2-trichloroethyl chloroformate, [4-(1,2,4-oxadiazol-3-yl)phenyl]thiocarbamic acid, 2,2,2-trichloroethyl ester is obtained.

EXAMPLES 7–26

[4-(1,2,4-Oxadiazol-3-yl)phenyl]carbamic or thiocarbamic acid, esters

Following the procedure of example 1 but substituting for the methyl chloroformate in part (d) an equivalent amount of the following:

isopropyl chloroformate
isopropyl chlorothioformate
allyl chloroformate
allyl chlorothioformate
2-propynyl chloroformate
2-propynyl chlorothioformate
cyclopropyl chloroformate
cyclopropyl chlorothioformate
cyclohexyl chloroformate
cyclohexyl chlorothioformate
4-fluorophenyl chloroformate
4-fluorophenyl chlorothioformate
4-methylphenyl chloroformate
4-methoxyphenyl chlorothioformate
4-nitrophenyl chloroformate
2,5-dichlorophenyl chloroformate
trifluoromethyl chloroformate
trifluoromethyl chlorothioformate
3-bromopropyl chloroformate
t-butyl chlorothioformate one obtains
[4-(1,2,4-oxadiazol-3-yl)phenyl]carbamic acid, isopropyl ester,
[4-(1,2,4-oxadiazol-3-yl)phenyl]thiocarbamic acid, isopropyl ester,
[4-(1,2,4-oxadiazol-3-yl)phenyl]carbamic acid, allyl ester,
[4-(1,2,4-oxadiazol-3-yl)phenyl]thiocarbamic acid, allyl ester,
[4-(1,2,4-oxadiazol-3-yl)phenyl]carbamic acid, 2-propynyl ester,
[4-(1,2,4-oxadiazol-3-yl)phenyl]thiocarbamic acid, 2-propynyl ester,
[4-(1,2,4-oxadiazol-3-yl)phenyl]carbamic acid, cyclopropyl ester,
[4-(1,2,4-oxadiazol-3-yl)phenyl]thiocarbamic acid, cyclopropyl ester,
[4-(1,2,4-oxadiazol-3-yl)phenyl]carbamic acid, cyclohexyl ester,
[4-(1,2,4-oxadiazol-3-yl)phenyl]thiocarbamic acid, cyclohexyl ester,
[4-(1,2,4-oxadiazol-3-yl)phenyl]thiocarbamic acid, 4fluorophenyl ester,
[4-(1,2,4-oxadiazol-3-yl)phenyl]thiocarbamic acid, 4-fluorophenyl ester,
[4-(1,2,4-oxadiazol-3-yl)phenyl]carbamic acid, 4-methylphenyl ester,
[4-(1,2,4-oxadiazol-3-yl)phenyl]thiocarbamic acid, 4-methoxyphenyl ester,
[4-(1,2,4-oxadiazol-3-yl)phenyl]carbamic acid, 4-nitrophenyl ester,
[4-(1,2,4-oxadiazol-3-yl)phenyl]carbamic acid, 2,5-dichlorophenyl ester,
[4-(1,2,4-oxadiazol-3-yl)phenyl]carbamic acid, trifluoromethyl ester,
[4-(1,2,4-oxadiazol-3-yl)phenyl]thiocarbamic acid, trifluoromethyl ester,
[4-(1,2,4-oxadiazol-3-yl)phenyl]carbamic acid, 3-bromopropyl ester,
and [4-(1,2,4-oxadiazol-3-yl)phenyl]thiocarbamic acid, t-butyl ester, respectively.

EXAMPLES 27–33

[Substituted-(1,2,4-oxadiazol-3-yl)phenyl]carbamic acid, methyl ester

Following the procedure of example 1a, but substituting for the p-nitrobenzonitrile an equivalent amount of the following:

2-nitro-3-methylbenzonitrile
3-nitro-2-chlorobenzonitrile
4-nitro-3-trifluoromethylbenzonitrile
4-nitro-2-ethoxybenzonitrile
2-nitro-4-phenylbenzonitrile
2-nitro-4-phenoxybenzonitrile
2-nitro-4-dimethylaminobenzonitrile one obtains 2-nitro-3-methylbenzamidoxime,
3-nitro-2-chlorobenzamidoxime,
4-nitro-3-trifluoromethylbenzamidoxime,
4-nitro-2-ethoxybenzamidoxime,
2-nitro-4-phenylbenzamidoxime,
2-nitro-4-phenoxybenzamidoxime,
and 2-nitro-4-dimethylaminobenzamidoxime.

By following the procedures of example 1b and c the following compounds of formula I are obtained:
[6-methyl-2-(1,2,4-oxadiazol-3-yl)phenyl]carbamic acid, methyl ester,

[2-chloro-3-(1,2,4-oxadiazol-3-yl)phenyl]carbamic acid, methyl ester,
[2-trifluoromethyl-4-(1,2,4-oxadiazol-3-yl)phenyl]carbamic acid, methyl ester,
[3-ethoxy-4-(1,2,4-oxadiazol-3-yl)phenyl]carbamic acid, methyl ester,
[5-phenyl-2-(1,2,4-oxadiazol-3-yl)phenyl]carbamic acid, methyl ester,
[5-phenoxy-2-(1,2,4-oxadiazol-3-yl)phenyl]carbamic acid, methyl ester,
and [5-dimethylamino-2-(1,2,4-oxadiazol-3-yl)phenyl]carbamic acid, methyl ester respectively.

Similarly, but substituting for the methyl chloroformate in the above examples the chloroformates and chlorothioformates of examples 2 to 26, other compounds within the scope of formula I are obtained.

EXAMPLE 34

[4-(5-Phenyl-1,2,4-oxadiazol-3-yl)phenyl]carbamic acid, methyl ester a. 5-Phenyl-3-(4-nitrophenyl)-1,2,4-oxadiazole

A solution of 10.8 g. (0.06 mole) of p-nitrobenzamidoxime and 8.5 g. (0.06 mole) of benzoyl chloride in 250 ml. of dioxane is heated on a steam bath for one hour, followed by the addition of 2 ml. of $BF_3$-$Et_2O$. After refluxing the solution overnight, the reaction mixture is cooled and the material which precipitates is collected by filtration to yield 8.1 g. (50%) of 5-phenyl-3-(4-nitrophenyl)-1,2,4-oxadizole.

b. 5-Phenyl-3-(4-aminophenyl)-1,2,4-oxadiazole

A suspension of 5.0 g. (0.02 mole) of 5-phenyl-3-(4-nitrophenyl)-1,2,4-oxadiazole, from part (a), in 200 ml. of 95% ethanol containing 0.5 g. of 5% Pd/C and 3ml. of concentrated HCl is hydrogenated on the Parr hydrogenator at 50 psi. over a period of 1 hour. The catalyst is removed by filtration followed by removal of the ethanol by distillation in vacuo to yield the 5-phenyl-3-(4-aminophenyl)-1,2,4-oxadiazole.

c. [4-(5-Phenyl-1,2,4-oxadiazol-3-yl)phenyl]carbamic acid, methyl ester 1.4 g. (0.015 mole) of methyl chloroformate is added to a mixture of 2.4 g. (0.01 mole) of 5-phenyl-3-(4-aminophenyl)-1,2,4-oxadiazole, from part (b), and 2.1 g. of potassium carbonate in 50 cc. of dioxane. The resulting mixture is refluxed for 0.5 hours. It is then concentrated to dryness and the residue is crystallized from benzene to yield [4-(5-phenyl-1,2,4-oxadiazol-3-yl)phenyl]carbamic acid, methyl ester.

EXAMPLES 35–44

[4-(5-Substituted-1,2,4-oxadiazol-3-yl)phenyl]carbamic acid, methyl ester

Following the procedure of example 34 but substituting for the benzoyl chloride in part (a) an equivalent amount of the following:

4-chlorobenzoyl chloride
3,4,5-trimethoxybenzoyl chloride
2-bromobenzoyl chloride
4-fluorobenzoyl chloride
3-ethylbenzoyl chloride
4-trifluoromethylbenzoyl chloride
cyclopropylcarboxylic acid chloride
cyclohexylcarboxylic acid chloride
acetyl chloride
butyryl chloride one obtains

[4-[5-(4-chlorophenyl)-1,2,4-oxadiazol-3-yl]phenyl]-carbamic acid, methyl ester,
[4-[5-(3,4,5-trimethoxyphenyl)-1,2,4-oxadiazol-3-yl]-phenyl]carbamic acid, methyl ester,
[4-[5-(2-bromophenyl)-1,2,4-oxadiazol-3-yl]phenyl]-carbamic acid, methyl ester,
[4-[5-(4-fluorophenyl)-1,2,4-oxadiazol-3-yl]phenyl]-carbamic acid, methyl ester,
[4-[5-(3-ethylphenyl)-1,2,4-oxadiazol-3-yl]phenyl]-carbamic acid, methyl ester, [4-[5-(4-trifluoromethylphenyl)-1,2,4-oxadiazol-3-yl]-phenyl]carbamic acid, methyl ester,
[4-(5-cyclopropyl-1,2,4-oxadiazol-3-yl)phenyl]-carbamic acid, methyl ester,
[4-(5-cyclohexyl-1,2,4-oxadiazol-3-yl)phenyl]-carbamic acid, methyl ester,
[4-(5-methyl-1,2,4-oxadiazol-3-yl)phenyl]carbamic acid, methyl ester,
and [4-(5-propyl-1,2,4-oxadiazol-3-yl)phenyl]carbamic acid, methyl ester, respectively.

Similary, by substituting for the methyl chloroformate in examples 34 to 44 the chloroformates and chlorothioformates of examples 2 to 26 and by also substituting for the p-nitrobenzamidoxime in part (a) of example 34 the substituted benzamidoximes of examples 27 to 33, other compounds within the scope of formula I are obtained.

EXAMPLE 45

[4-[5-(2-Pyridyl)-1,2,4-oxadiazol-3-yl]phenyl]carbamic acid, methyl ester a. 5-(2-Pyridyl)-3-(4-nitrophenyl)-1,2,4-oxadiazole

To a solution of 3.6 g. (0.02 mole) of p-nitrobenzamidoxime in 250 ml. dioxane there is added 4.0 g. of picolinic acid chloride and the mixture is stirred at room temperature for 5 minutes until a precipitate is formed. After the addition of 0.5 ml. of $BF_3$-$Et_2O$, the mixture is refluxed for 18 hours. The precipitate which forms upon cooling is filtered off, dried and crystallized from EtOH to yield 3.2 g. (60%) of 5-(2-pyridyl)-3-(4-nitrophenyl)-1,2,4-oxadiazole; m.p. 202°–203°.

b. 5-(2-Pyridyl)-3-(4-aminophenyl)-1,2,4-oxadiazole

A mixture of 2.68 g. (0.01 mole) of 5-(2-pyridyl)-3-(4-nitrophenyl)-1,2,4-oxadiazole, from part (a), 10 ml. of 10% HCl, 190 ml. of absolute ethanol, and 0.27 g. of 5% Pd/C is reduced on the Parr hydrogenator at 50 psi. until the required amount of hydrogen is absorbed. The catalyst is removed by filtration followed by removal of the ethanol by distillation in vacuo to yield the 5-(2-pyridyl)-3-(4-aminophenyl)-1,2,4-oxadiazole.

c. [4-[5-(2-Pyridyl)-1,2,4-oxadiazol-3-yl]phenyl]-carbamic acid, methyl ester 1.4 g. (0.015 mole) of methyl chloroformate is added to a mixture of 2.4 g. (0.01 mole) of 5-(2-pyridyl)-3-(4-aminophenyl)-1,2,4-oxadiazole, from part (b), and 2.1 g. of potassium carbonate in 50 cc. of dioxane. The resulting mixture is refluxed for 0.5 hours. It is then concentrated to dryness and the residue is crystallized from benzeneethyl acetate to yield [4-[5-(2-pyridyl)-1,2,4-oxadiazol-3-yl]-phenyl]carbamic acid, methyl ester.

EXAMPLES 46–53

[4-(5-Heterocyclic)-1,2,4-oxadiazol-3-yl)phenyl]carbamic acid, methyl ester

Following the procedure of Example 45 but substituting for the picolinic acid chloride in part (a) an equivalent amount of the following:

nicotinic acid chloride
isonicotinic acid chloride
2-thiophenecarboxylic acid chloride
4-thiazolecarboxylic acid chloride
2-furoyl chloride
3-furoyl chloride
N-methylpyrrole-2-carboxylic acid chloride
N-methylpyrrole-3-carboxylic acid chloride one obtains

[4-[5-(3-pyridyl)-1,2,4-oxadiazol-3-yl]phenyl]carbamic acid, methyl ester
[4-[5-(4-pyridyl)-1,2,4-oxadiazol-3-yl]phenyl]carbamic acid, methyl ester,
[4-[5-(2-thienyl)-1,2,4-oxadiazol-3-yl]phenyl]carbamic acid, methyl ester,
[4-[5-(4-thiazole)-1,2,4-oxadiazol-3-yl]phenyl]carbamic acid, methyl ester,
[4-[5-(2-furyl)-1,2,4-oxadiazol-3-yl]phenyl]carbamic acid, methyl ester,
[4-[5-(3-furyl)-1,2,4-oxadiazol-3-yl]phenyl]carbamic acid, methyl ester,
[4-[5-(N-methyl-2-pyrrole)-1,2,4-oxadiazol-3-yl]phenyl]-carbamic acid, methyl ester,
and [4-[5-(N-methyl-3-pyrrole)-1,2,4-oxadiazol-3-yl]phenyl]-carbamic acid, methyl ester, respectively.

Similarly, by substituting for the methyl chloroformate in examples 45 to 53 the chloroformates and chlorothioformates of examples 2 to 26 and also by substituting for the p-nitrobenzamidoxime in part (a) of example 45 the substituted benzamidoximes of examples 27 to 33, other compounds within the scope of formula I are obtained.

What is claimed is:

1. A compound of the formula

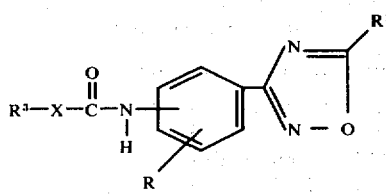

wherein X is oxygen or sulfur; R is selected from the group consisting of hydrogen, lower alkyl, phenyl, chloro, bromo, lower alkoxy, trifluoromethyl, phenoxy, and di(lower alkyl)-amino; $R^1$ is selected from the group consisting of hydrogen, lower alkyl, cycloalkyl of 3 to 6 carbons, phenyl, and substituted-phenyl; and $R^3$ is selected from the group consisting of lower alkyl, substituted-lower alkyl, lower alkenyl, lower alkynyl; cycloalkyl of 3 to 6 carbons, phenyl and substituted phenyl; said phenyl substituent being one or two members selected from the group consisting of fluoro, chloro, bromo, iodo, nitro, amino, trifluoromethyl, lower alkyl, and lower alkoxy or trimethoxy and said lower alkyl substituent being one or more members selected from the group consisting of chloro, bromo, fluoro and iodo; and the pharmaceutically acceptable salts thereof.

2. The compound of claim 1 wherein R is hydrogen or chlorine; and $R^1$ is selected from the group consisting of hydrogen, lower alkyl, cycloaklyl of 3 to 6 carbons, phenyl and substituted-phenyl.

3. The compound of claim 2 wherein R is hydrogen; $R^1$ is selected from the group consisting of hydrogen, cyclopropyl, cyclohexyl, phenyl, 4-chlorophenyl, and 3,4,5-trimethoxyphenyl; and $R^3$ is selected from the group consisting of alkyl of 1 to 4 carbons, phenyl, substituted-phenyl, and substituted-alkyl of 1 to 4 carbons wherein said alkyl substituent is one, two, or three chloro, bromo, or fluoro groups, alkenyl of 2 to 4 carbons, and alkynyl of 2 to 4 carbons.

4. A compound of the formula

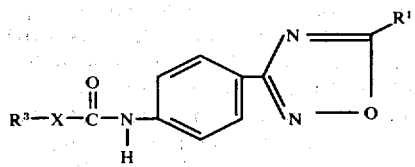

wherein X is oxygen or sulfur; $R^1$ is selected from the group consisting of hydrogen, lower alkyl, cycloalkyl of 3 to 6 carbons, phenyl, and substituted phenyl; and $R^3$ is selected from the group consisting of lower alkyl, lower alkenyl, lower alkynyl, substituted-lower alkyl, cycloalkyl of 3 to 6 carbons, phenyl, and substituted phenyl; said phenyl substituent being one or two members selected from the group consisting of fluoro, chloro, bromo, iodo, nitro, amino, trifluoromethyl, lower alkyl and lower alkoxy or trimethoxy and said lower alkyl substituent being one or more members selected from the group consisting of chloro, bromo, fluoro, and iodo; and the pharmaceutically acceptable salts thereof.

5. The compound of claim 4 wherein $R^1$ is selected from the group consisting of hydrogen, cyclopropyl, cyclohexyl, phenyl, 4-chlorophenyl, and 3,4,5-trimethoxyphenyl; and $R^3$ is selected from the group consisting of alkyl of 1 to 4 carbons, alkenyl of 2 to 4 carbons, alkynyl of 2 to 4 carbons, cycloalkyl of 3 to 6 carbons, phenyl, substituted-phenyl, and substituted alkyl of 1 to 4 carbons wherein said alkyl substituent is one, two, or three chloro, bromo, or fluoro groups.

6. The compound of claim 5 wherein $R^1$ is hydrogen and $R^3$ is selected from the group consisting of alkyl of 1 to 4 carbons, allyl, 2-propynyl, cyclopropyl, phenyl, 2,2,2-trichloroethyl, and 4-fluorophenyl.

7. The compound of claim 6 wherein X is oxygen and $R^3$ is methyl, phenyl, or 2,2,2-trichloroethyl.

8. The compound of claim 7 wherein $R^3$ is methyl.

9. The compound of claim 7 wherein $R^3$ is phenyl.

10. The compound of claim 7 wherein $R^3$ is 2,2,2-trichloroethyl.

* * * * *